United States Patent [19]

Trokel

[11] Patent Number: 5,471,262
[45] Date of Patent: Nov. 28, 1995

[54] APPARATUS AND METHOD TO MEASURE VISUAL FUNCTION UNDER SIMULATED NIGHTTIME CONDITIONS

[76] Inventor: Stephen L. Trokel, 190 E. 72nd St., New York, N.Y. 10021

[21] Appl. No.: 237,634

[22] Filed: May 4, 1994

[51] Int. Cl.⁶ .................................................... A61B 3/02
[52] U.S. Cl. ............................................ 351/239; 351/246
[58] Field of Search .................................. 351/211, 222, 351/237, 239, 243, 246; 128/665, 745; 606/204.25

[56] References Cited

U.S. PATENT DOCUMENTS

| | | | |
|---|---|---|---|
| 1,591,969 | of/0000 | Freeman | 251/243 |
| 1,795,752 | of/0000 | Bauersfeld et al. | 351/243 |
| 2,036,181 | of/0000 | Mendelsohn et al. | 351/243 |
| 3,328,113 | of/0000 | Dimmick et al. | 351/243 |
| 3,374,572 | 10/1965 | Course | 351/200 |
| 3,415,594 | of/0000 | Aulhorn | 351/243 |
| 3,425,772 | 2/1969 | Minas | 351/243 |
| 3,469,904 | 9/1969 | Allen | 251/243 |
| 3,684,355 | 8/1972 | Molner | 351/243 |
| 3,936,162 | 2/1976 | Kraukau et al. | 351/243 |
| 4,212,520 | 7/1980 | Klimsa | 351/243 |
| 4,239,351 | 12/1980 | Williams et al. | 351/243 |
| 4,379,699 | 4/1983 | Nelson | 351/239 |
| 4,403,842 | 9/1983 | Aulhorn et al. | 351/237 |
| 4,412,729 | 11/1983 | Hartmann | 351/239 |
| 4,550,990 | 11/1985 | Trispel et al. | 351/243 |
| 4,764,007 | 8/1988 | Task | 351/243 |
| 4,800,404 | 1/1989 | Ginsburg et al. | 351/243 |
| 4,998,820 | 3/1991 | Salibello et al. | 351/243 |
| 5,129,720 | 7/1992 | Jovicevic | 351/243 |
| 5,191,367 | 3/1993 | Salibello et al. | 351/243 |

*Primary Examiner*—William L. Sikes
*Assistant Examiner*—Huy Mai
*Attorney, Agent, or Firm*—Amster, Rothstein & Ebenstein

[57] ABSTRACT

An apparatus and method for measuring visual function under simulated nighttime conditions where the pupil is large by maintaining extremely low ambient illumination when the test is performed in a darkened room, the apparatus including a test field defining a plurality of recognizable indicia of variable irradiance which appear on a black background having zero irradiance, the test field being either transilluminated or illuminated by projection, and a field stop having a plurality of apertures of progressive sizes which are placed in front of the eye of the person being tested to ascertain the true functional optical zone of the cornea.

9 Claims, 5 Drawing Sheets

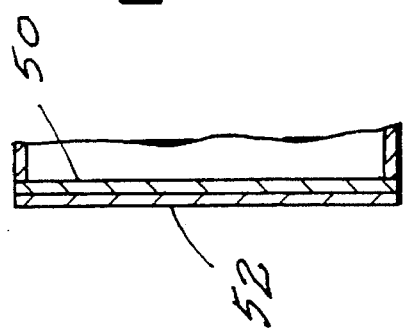
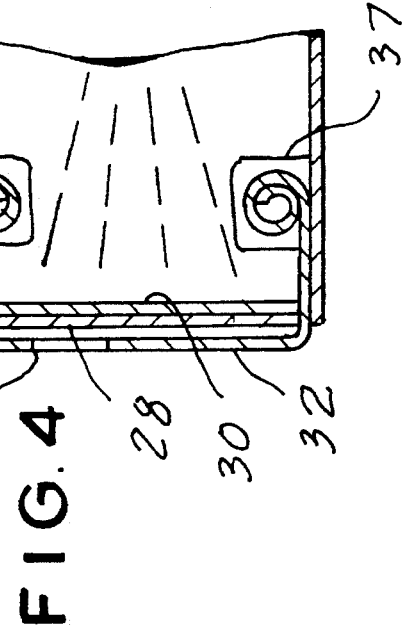
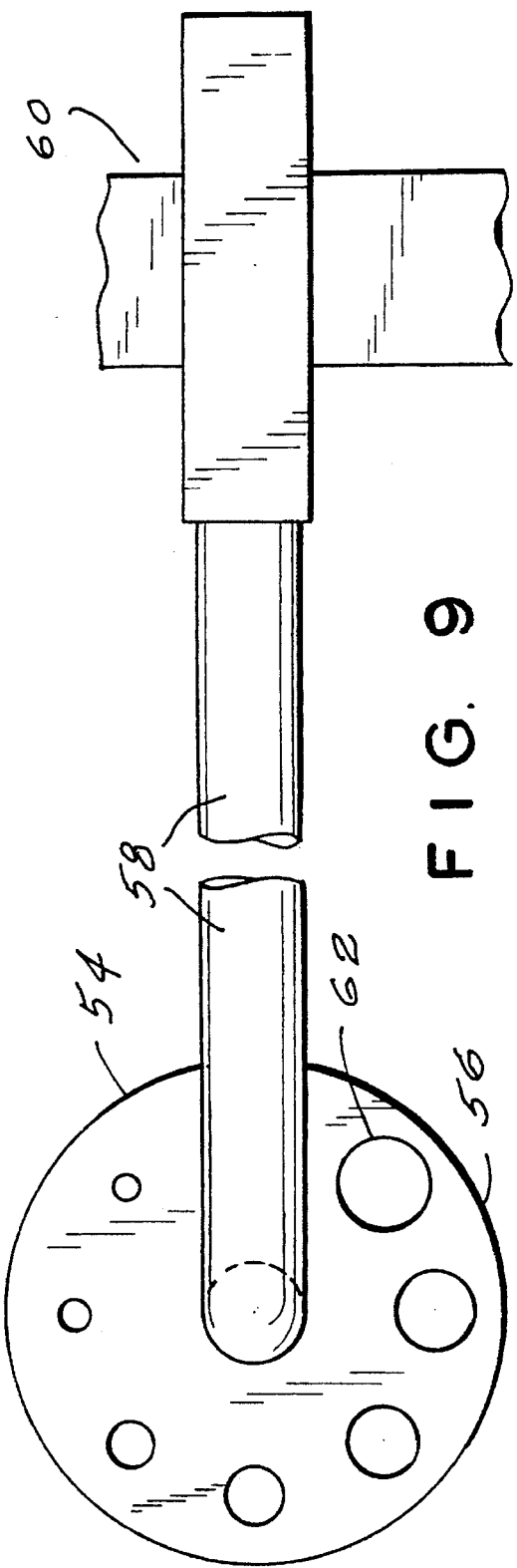

APPARATUS AND METHOD TO MEASURE VISUAL FUNCTION UNDER SIMULATED NIGHTTIME CONDITIONS

BACKGROUND

The present invention relates generally to testing visual acuity, and in particular, to an apparatus and method for accurately evaluating night vision after refractive surgical procedures.

It is well known that many people have difficulty seeing at night or during conditions of low ambient illumination. Those who engage in activities such as night driving or flying must be tested to determine visual acuity under simulated nighttime conditions. The prior art is replete with various devices and methods directed to that end.

An example can be found in U.S. Pat. No. 4,764,007 to Task, which relates to a glare susceptibility tester in which an acuity target having translucent recognizable indicia on an opaque background or opaque indicia on a translucent background, is transilluminated and presented to a person being tested with a side-by-side glare source for simultaneous viewing. The observed glare obscures a portion of the pattern of the acuity target to a degree corresponding to the person's susceptibility to glare. Visual function is determined for each of the targets with and without the glare source being selectively exposed such that diminution of visual performance as a result of glare can be determined.

U.S. Pat. No. 4,403,842 to Aulhorn et al. is directed to an apparatus for testing twilight vision and blinding sensitivity. The person being tested looks inside a housing to view a screen having a test figure which is illuminated by projection and a headlight simulating source disposed adjacent to the field of vision. The test figure includes indicia disposed on an outer field wherein the contrast between the outer field and the indicia may be varied to test twilight vision. Blinding sensitivity is tested by turning on the headlight source for short periods of time.

U.S. Pat. No. 3,684,355 to Molner is also directed to a method and apparatus for testing glare susceptibility where the person being tested views both a representative target contained on a film strip which is variably illuminated and a glare source of variable intensity.

U.S. Pat. No. 4,412,729 to Hartmann teaches a test field for providing test conditions resembling those to which the eye is subjected to when working with an electronic CRT terminal. The test field contains indicia such as characters or symbols which appear bright on a darker background and brighter areas of luminance on the order of five to ten times greater than the luminance of the indicia.

The prior art vision testing devices and methods such as those noted above have been found to be unsuitable for fully evaluating night vision after refractive surgical procedures. When refractive surgery is performed on the eye, a central portion of the cornea less than the entire structure is modified, thereby reducing the effective optical area. Existing night vision tests, especially those developed for testing glare susceptibility, typically provide an overall level of illumination sufficient to cause the pupil to become small or moderately sized. While this can be advantageous in replicating actual conditions such as, for example, those encountered during exposure to headlights when driving at night, there are also nighttime conditions under which the ambient illumination is sufficiently low to cause the pupil to become large. Thus, after refractive surgical procedures, a small pupil under test conditions can render determination of visual function inaccurate because under actual nighttime conditions the true pupil size may be large enough to include portions of the cornea which may not have been modified to the new optical state.

It is therefore an object of the present invention to provide a method and apparatus for measuring visual function under simulated nighttime conditions when the pupil is large.

It is yet another object of the present invention to provide a method for measuring visual function under simulated nighttime conditions where the test field is placed at the far field of the eye to minimize pupillary constriction.

It is yet another object of the present invention to provide an apparatus for measuring night visual function under simulated nighttime conditions in which a test field provides a bright resolution acuity target while maintaining extremely low ambient illumination.

It is still another object of the present invention to provide an apparatus and method for measuring visual function under simulated nighttime conditions where the cone of light entering the eye may be artificially limited to ascertain the true functional optical zone of the cornea.

SUMMARY OF THE INVENTION

In accordance with the above objects and additional objects which will become apparent hereinafter, the present invention provides an apparatus and method for measuring visual function under simulated nighttime conditions where the pupil is large, especially useful following refractive surgical procedures.

The apparatus includes a test field having recognizable indicia of variable irradiance which appear on a black background of zero irradiance. This arrangement provides a bright resolution target, yet maintains extremely low ambient illumination. The high relative irradiance of the letters causes rapid degradation in night visual acuity if there is a multifocal cornea, haze or a displaced optical zone. The indicia may comprise, but are not limited to, a graded series of letters, tumbling E's or the like, which are comparable to Snellen letters in size and resolution separation.

In a preferred embodiment, the test field includes a panel having a front surface and a rear surface where the front surface is totally black and exposed to the person being tested. The panel has a plurality of apertures therethrough defining the various indicia and is oriented with the rear surface thereof disposed against a diffusive screen to provide a translucent background behind the indicia. The panel and screen are attached to a housing having a light source therein for transilluminating the indicia and the irradiance of the indicia may be varied by controlling the intensity of the light source. A screen for isolating a single line or symbol of the indicia may be incorporated. To maximize dilation of the pupil and minimize other recognition clues which the patient may adopt in an attempt to screen-out any glare, the indicia can be illuminated for a predetermined length of time (typically some fraction of a second).

In order to determine the true functional optical zone of the cornea, a field stop may be used to artificially limit the cone of light viewed by the person being tested. The field stop defines a plurality of apertures of progressive sizes therethrough which are placed directly in front of the eye and functioning as artificial pupils. By adjusting the field stop to selectively change the aperture size during testing, the cone of light entering the eye can be restricted or enlarged to enable the examiner to determine the degree of visual impairment when the enlarged pupil encompasses portions of the cornea which may have not been modified to a new optical state following refractive surgery.

The present invention also contemplates a method for performing eye examinations under simulated nighttime conditions comprising the following series of steps:

(a) providing a test field of recognizable indicia of variable irradiance which appear on a zero-irradiance black background in a darkened room;

(b) positioning a person to be tested in the darkened room relative to said test field;

(c) varying the irradiance of the indicia;

(d) having the person identify the indicia; and (e) measuring the quality of vision under varying test conditions.

To accurately simulate conditions which may be encountered during activities such as night driving, it will be appreciated that the advantages of the test described herein are realized by positioning the person to be tested at a sufficient distance from the test field, what is generally referred to as the "far field of the eye." The far field of the eye, as defined herein, refers to distances between the test subject and the test field of at least 15 feet to minimize pupillary constriction.

In an additional step to determine the true functional optical zone of the cornea, a field stop as described above may be placed directly in front of the eye. The apertures defined in the field stop provide artificial pupils of progressive diameter which are selectable by the examiner to limit the cone of light entering the eye. The Examiner can vary the size and location of the stop apertures relative to the eye until visual acuity has improved to normal levels.

BRIEF DESCRIPTION OF THE DRAWINGS

FIG. 4 is a sectional view along lines 4—4 in FIG. 2;

FIG. 8 is a sectional view along lines 8—8 in FIG. 7 showing the construction of a test field for illumination by projection; and FIG. 9 is a front elevational view of a field stop.

DETAILED DESCRIPTION OF THE PREFERRED EMBODIMENT

With reference to the several views of the drawings, there is depicted an apparatus and method for testing visual function under simulated nighttime conditions.

Figure 1:
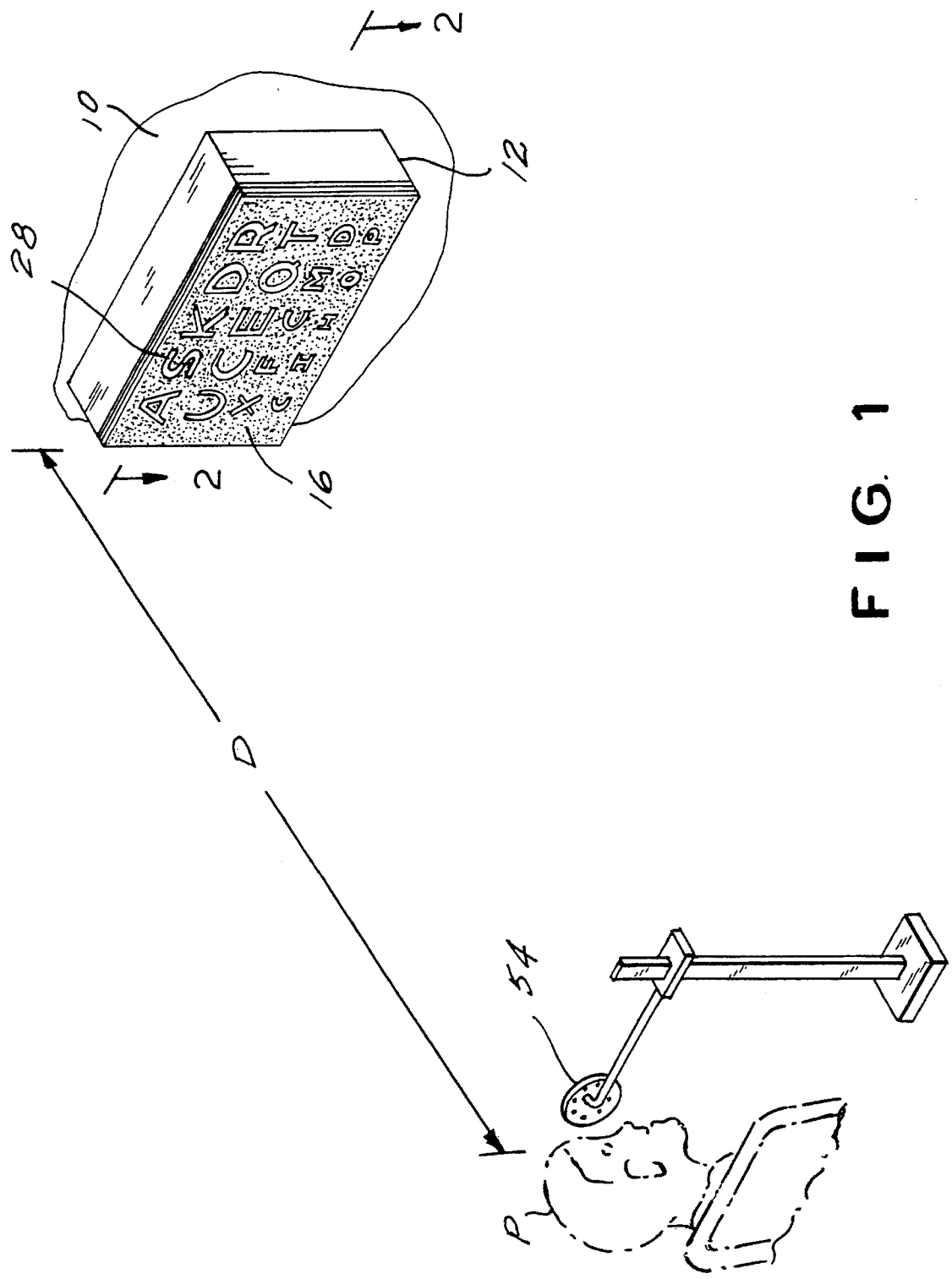
FIG. 1 is an isometric view of a representative test apparatus as viewed by a person being tested.

Referring now to FIG. 1, a person being tested ("test subject P") is positioned relative to a testing apparatus 10. It has been found that more realistic simulations of actual nighttime conditions encountered during activities such as night driving can be made by testing in the far field to minimize pupillary constriction. Accordingly, the best results have been obtained by displacing test subject P from apparatus 10 by a distance D of at least 15 feet or greater.

With reference to FIGS. 1–4, in a preferred, albeit illustrative embodiment, tester 10 consists of a housing 12 (shown schematically) which contains an illumination source 14 for uniformly transilluminating a test field 16. It is anticipated that illumination source 14 may be selected from a variety of types known in the art such as incandescent, panelescent, flourescent and the like. It has been found that parallel flourescent lights assure a uniform distribution of light to transilluminate the optotypes. Illumination source 14 is electrically connected to a power source 18 and a controller 20 which permits the Examiner to vary the degree of illumination.

Figure 3:
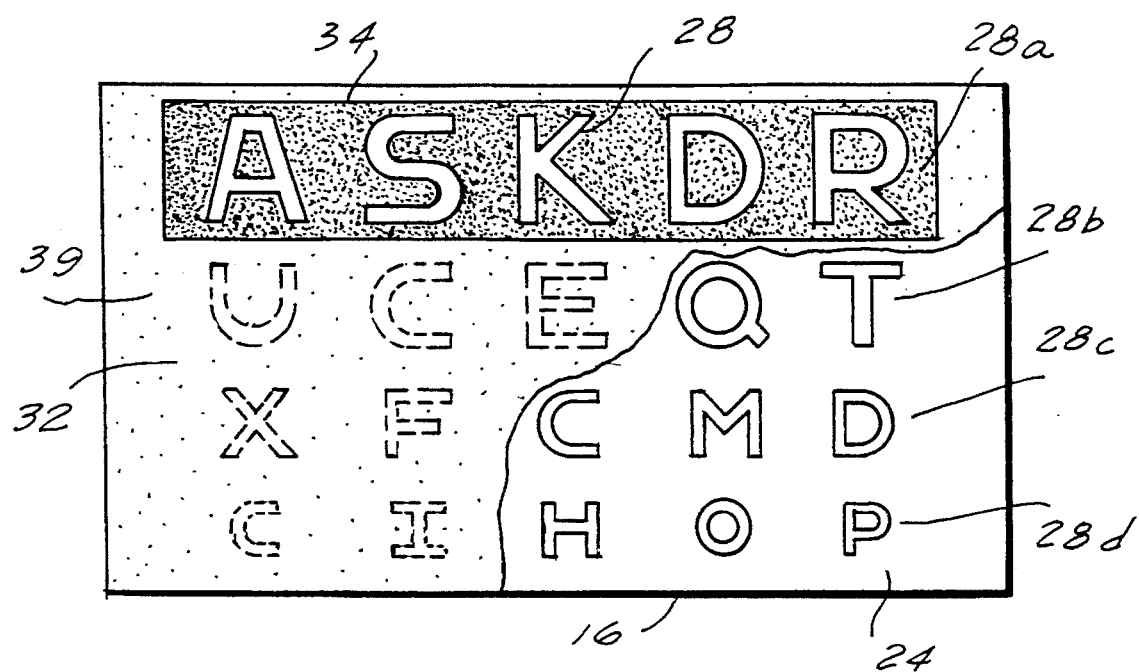
FIG. 3 is a front elevational view of the test field and a screen for isolating a single row of the test field indicia.
Figure 5:
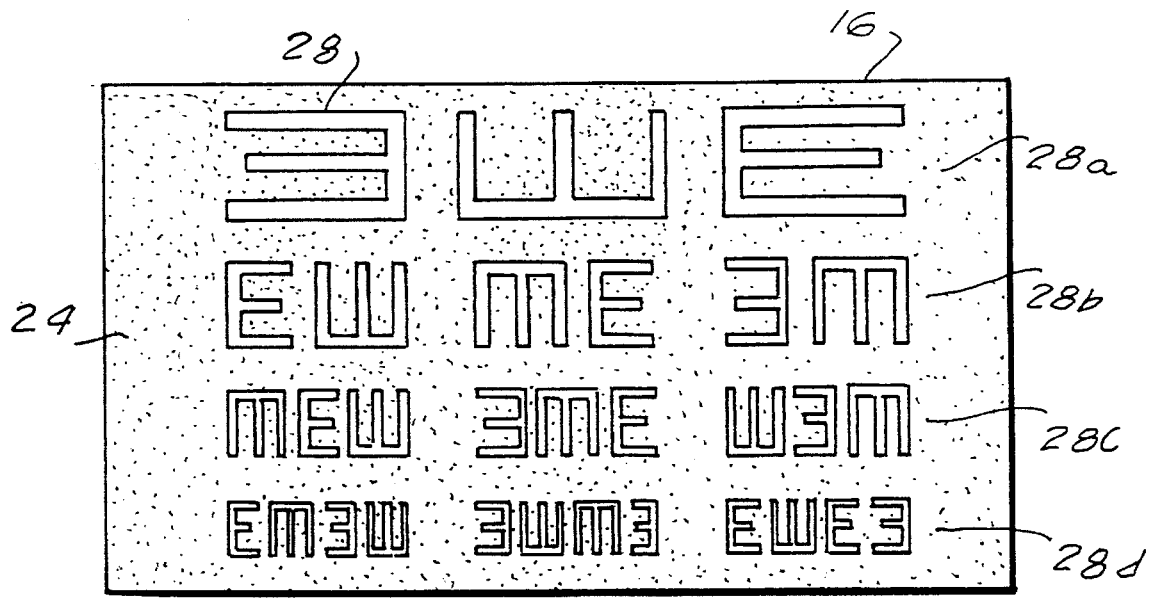
FIG. 5 is a front elevational view of an alternative embodiment of the test field indicia.

Test field 16 consists of a panel 22 having a front surface 24 and a rear surface 26. Panel 22 is preferably metal, but may be constructed from other materials such as plastic. A plurality of apertures or cutouts are defined in panel 22 to form recognizable indicia 28. Indicia 28 may be arranged in any predetermined pattern, the preferred embodiment having a graded series of letters in multiple rows 28a, 28b, 28c, 28d and 28e which are comparable to Snellen letters in size and resolution separation as shown in FIG. 3, or the well-known "tumbling E" design as depicted in FIG. 5. Of course, other indicia types and patterns may be used within the scope of the invention, the depicted embodiments being exemplary.

In order to ensure that the pupil is large by maintaining extremely low ambient illumination during the testing procedure, the side of panel 22 exposed to the test subject P and for purposes of convenience identified as front surface 24, is colored completely black in its entirety where it forms the boundaries of indicia 28. By "completely black", front surface 24 is said to have zero irradiance. It has been found that this arrangement provides a bright resolution target yet does not cause the pupil to become small during the test.

Figure 2:
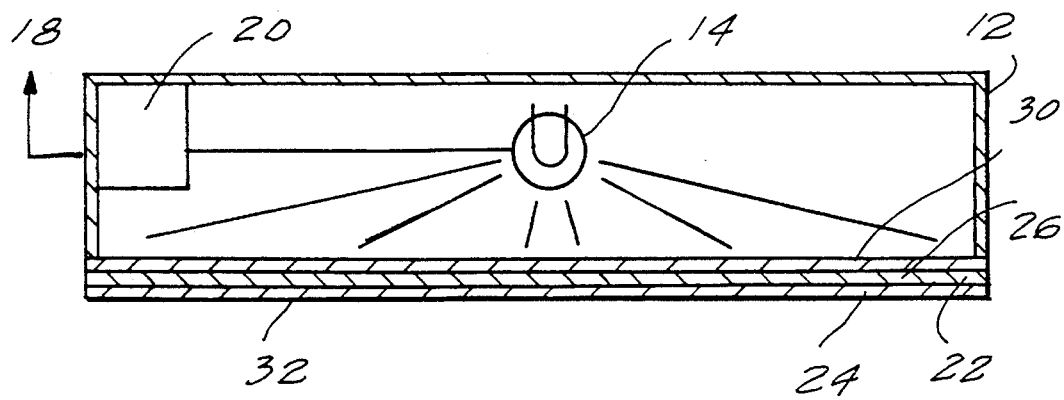
FIG. 2 is a sectional view along lines 2—2 in FIG. 1, schematically showing the arrangement of the test field and optical components.

Panel 22 is positioned with rear surface 26 thereof against a diffusive screen or layer 30 forming a translucent background for indicia 28. Light emanating from illumination source 14 passes through diffusive screen 30 to uniformly illuminate indicia 28. As shown in FIGS. 2–4 (omitted from FIG. 1 for clarity), a screen 32 may also be incorporated to isolate a single line of indicia 28 for viewing. Screen 32 contains a window 34 which selectively exposes a row of indicia 28 when screen 32 is translated either up or down by appropriate means 37 as shown in FIG. 4. The exposed surface 39 of screen 32 is also completely black so as to have zero irradiance.

Figure 6:
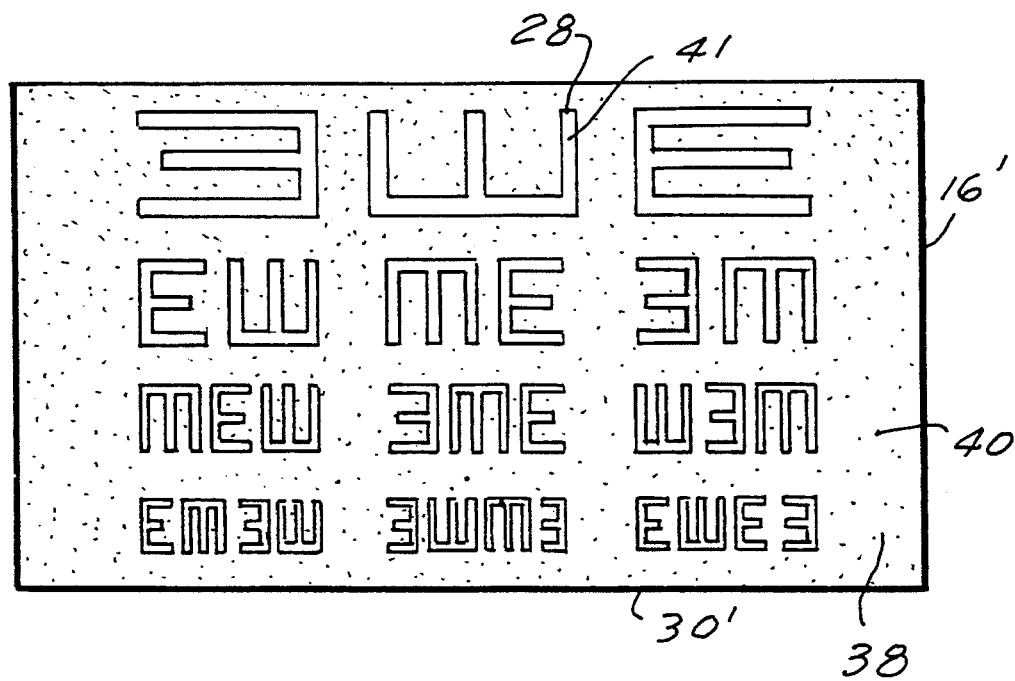
FIG. 6 is a front elevational view of an alternative embodiment of the test field construction.

As depicted in FIG. 6, a test field 16' may be alternatively constructed from a single layer of diffusive material 30' by applying a light-absorbing, totally black coating 38 on the front surface 40 thereof in a pattern to form transparent areas 41 defining the various indicia 28.

Figure 7:
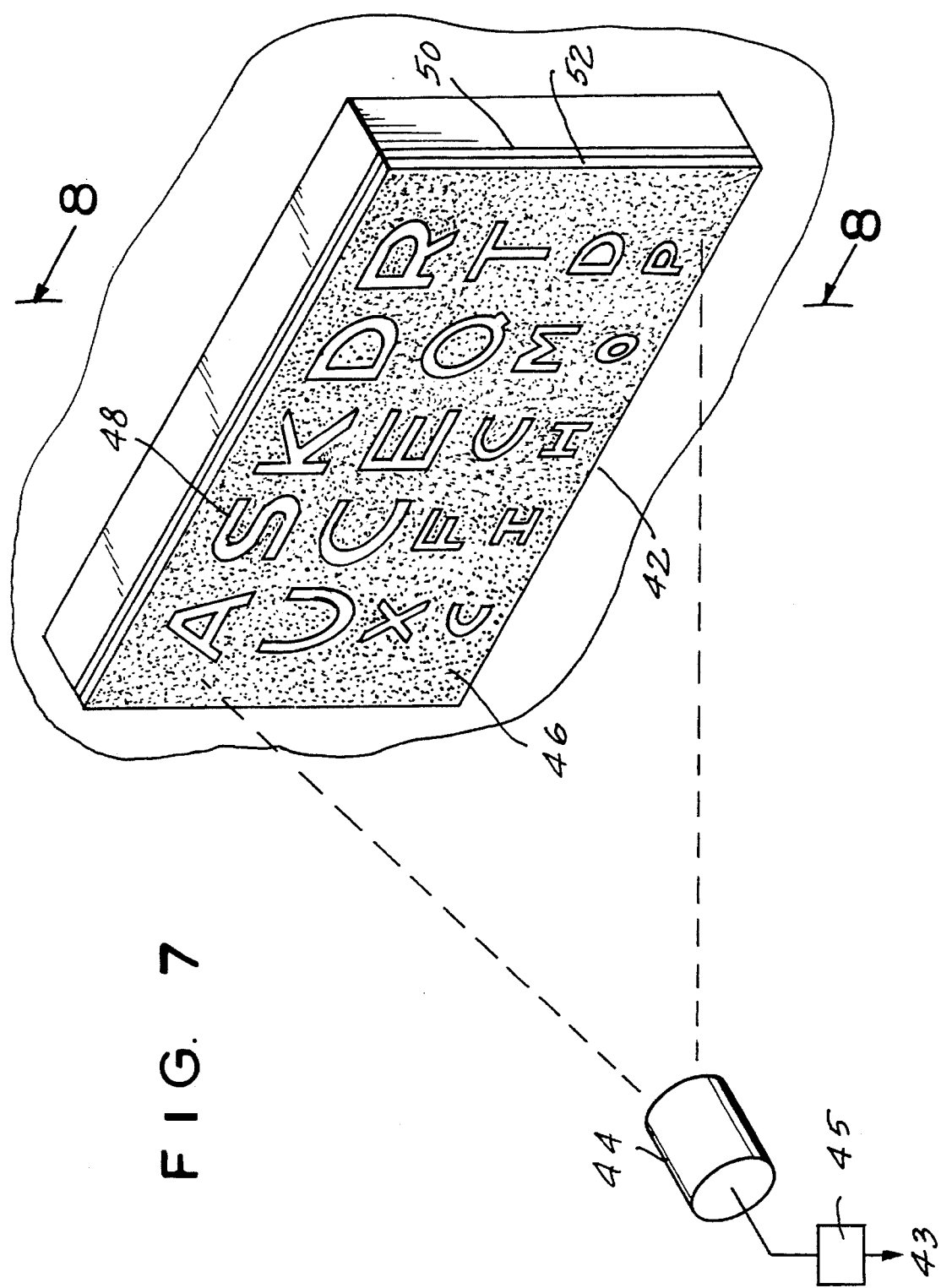
FIG. 7 is an isometric view schematically depicting a projection arrangement.

The invention is not limited to a transilluminated test field. FIG. 7 is a schematic of an alternative embodiment in which a test field 42 is illuminated by a projector apparatus 44. Test field 42 includes a totally black background 46 against which a plurality of recognizable indicia 48 are defined. As shown in FIG. 8, indicia 48 may be formed by overlaying a reflective sheet 50 with a panel 52 having a plurality of apertures or cutouts. Projector apparatus 44 projects a beam of light on the reflective sheet 50 to cause the indicia to become visible. Projector 44 is electrically connected to a power source 43 and can include an appropriate controller 45 to vary the amount of light incident on the test field 42 to vary the irradiance of the indicia 48. The black background 46 absorbs the incident light to minimize ambient illumination while providing a bright resolution target for the test subject P. Alternatively, reflective sheet 50 can be coated with a totally black, light-absorbing material in a pattern defining the various indicia in a manner similar to the embodiment of FIG. 6.

Referring now to FIGS. 1 and 9, a field stop 54 can be used to artificially limit the cone of light reaching the eye. This is useful for determining the true functional optical zone of the cornea. Field stop 54 consists of a disc 56 rotatably mounted on a support member 58 which is attached to a support structure 60. The test subject P is proximately positioned relative to field stop 54 such that test subject P can observe the test field 16 through any one of a plurality of apertures 62 defined in disc 56 which simulate pupils of progressive diameter. Field stop 54 should be positioned such that the apertures 62 are in close proximity to the eye of the test subject P. Disc 56 and support member 58 can be provided with cooperating provisions (not shown) to lock disc 56 in place for each aperture position when aligned with test subject P's line of sight. Good results have been obtained using eight apertures 62 ranging in size from 3.0 mm to 6.5 mm in 0.5 mm increments. During the test, the examiner adjusts the field stop 54 by rotating disc 56 to change the aperture size and thus the incident cone of light viewed by the test subject P. In this manner, the size and location of the corneal optics may be determined. It will be appreciated that the field stop configuration shown in FIG. 9 and described above is merely exemplary. Alternatively, the field stop could consist of an elongated member having the variably sized apertures arranged in a side-by-side linear relationship.

In accordance with the present invention, the test subject P is positioned relative to testing apparatus 10 at a distance D of at least 15 feet or more from the test field 16. The testing is performed in an absolutely darkened room such that the only thing that the test subject P sees are the indicia 28 of the test field. Screen 32 may be adjusted so that only a single row of indicia 28 are exposed through window 34 at any given time. The examiner asks the patient to read each row of the indicia 28 starting with the largest (e.g., row 28a) at the top of test field 16. The examiner can vary the irradiance of indicia 28 by adjusting the intensity of illumination source 14 to simulate nighttime conditions of variable luminance. This procedure is repeated for successive rows and at variable degrees of illumination until test subject P is unable to identify the target. The Examiner can also illuminate the indicia for a predetermined length of time, either all rows simultaneously, or each one individually by using the screen 32 to isolate a single line 9, typically for some fraction of a second. Such selective exposure is advantageous by maximizing dilation of the pupil, minimizing other maneuvers that the patient may adopt in an attempt to screen-out any glare, and preventing pupil constriction during testing.

As described above, field stop 54 can be positioned with apertures 62 located directly in front of the test subject P to provide a plurality of artificial pupils. In this manner, the examiner can selectively limit the cone the light reaching the eye to simulate enlarging or contracting the pupil. By rotating disc 56 to adjust the aperture size 62, the size and location of the corneal optics may be determined. This procedure can be repeated when viewing each row of indicia 28 under variable conditions of illumination.

The present invention has been shown and described in what is considered to be the most practical and preferred embodiment. It is anticipated, however, that departures may be made therefrom and that obvious modifications will occur to persons skilled in the art.

I claim:

1. An apparatus for testing visual function of a person following refractive surgical procedures where the corneal optics have been modified, under simulated nighttime conditions when the pupil is large, comprising:

a test field having recognizable indicia of variable irradiance which appear on a light absorbing, completely black background having substantially zero irradiance to maximize pupillary size during the test;

whereby said indicia of variable irradiance provide a bright resolution target for the person being tested while said black background of substantially zero-irradiance maintains extremely low ambient illumination when the test is performed in a darkened room.

2. The apparatus for testing visual function recited in claim 1, wherein said indicia of variable irradiance are transilluminated.

3. The apparatus for testing visual function recited in claim 1, wherein said indicia of variable irradiance are illuminated by projection.

4. The apparatus for testing visual function recited in claim 1, wherein said test field indicia comprises a graded series of letters comparable to Snellen letters in size and resolution separation.

5. The apparatus for testing visual function recited in claim 1, further comprising a field stop defining a plurality of apertures of progressive sizes therethrough for artificially limiting the cone of light viewed by the person being tested to ascertain the true functional optical zone of the cornea.

6. A method for testing visual function of a person following refractive surgical procedures where the corneal optics have been modified, under simulated nighttime conditions when the pupil is large, comprising the steps of:

(a) providing a test field of recognizable indicia of variable irradiance which appear on a light absorbing, completely black background having substantially zero irradiance in a darkened room to maximize pupillary size during the test;

(b) positioning a person to be tested in said darkened room relative to said test field;

(c) varying the irradiance of said indicia;

(d) having said person identify said indicia; and (e) measuring the quality of vision under varying test conditions.

7. The method for testing visual function recited in claim 6, further comprising the step of placing a field stop in front of an eye of said person being tested to artificially vary the incident cone of light by simulating pupils of progressive diameter to ascertain the true functional optical zone of the cornea.

8. The method for testing visual function recited in claim 6, wherein said person to be tested is positioned at least 15 feet from said test field such that said test field is at the far field of the eye.

9. The method for testing visual function recited in claim 6, wherein step (c) further includes illuminating said indicia, at least in part, for a predetermined length of time.

\* \* \* \* \*